(12) United States Patent
Strehler

(10) Patent No.: US 7,069,778 B1
(45) Date of Patent: Jul. 4, 2006

(54) FIXTURE FOR TESTING SPRING SQUARENESS UNDER A LOAD

(75) Inventor: Richard E Strehler, Bremen, IN (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/906,150

(22) Filed: Feb. 4, 2005

(51) Int. Cl.
*G01L 1/04* (2006.01)

(52) U.S. Cl. .............................. 73/161; 73/818; 33/535
(58) Field of Classification Search ................... 33/535; 73/161, 818
See application file for complete search history.

(56) References Cited

U.S. PATENT DOCUMENTS

| | | | | |
|---|---|---|---|---|
| 1,565,519 A | * | 12/1925 | Spooner ..................... | 324/240 |
| 1,898,529 A | * | 2/1933 | Farmer ........................ | 73/161 |
| 2,568,596 A | * | 9/1951 | Ruge ........................... | 73/161 |
| 2,671,210 A | * | 3/1954 | Aviles ......................... | 73/161 |
| 2,784,588 A | * | 3/1957 | Humble et al. ............... | 73/161 |
| 3,206,971 A | * | 9/1965 | Ernst ..................... | 73/862.625 |
| 4,157,033 A | * | 6/1979 | Shereda et al. ............... | 73/161 |
| 4,472,882 A | | 9/1984 | Hutter | |
| 5,579,659 A | * | 12/1996 | Roberts ....................... | 73/168 |
| 5,832,774 A | * | 11/1998 | Smith .......................... | 73/161 |

\* cited by examiner

*Primary Examiner*—Yaritza Guadalupe-McCall
(74) *Attorney, Agent, or Firm*—Leo H McCormick Jr.; Sarah Taylor

(57) ABSTRACT

A fixture and technique for testing a coil spring selected from a supply of springs. Each spring has an unstressed generally helical configuration and the test determines an excess departure from the helical configuration of a spring under a compressive load. The first end of a selected spring is radially fixed in a first guide while a second end of the spring end is axially retained in a movable second guide that is supported on rollers to allow omni-directional transverse radial motion of the second end. An axial compressive force is applied to the selected spring while allowing the second end relatively free radial motion. When compression induced radial motion of the second end exceeds a predetermined threshold, the second end the selected spring closes a normally opened electrical circuit to inform an operator that the selected spring is excessively out of square and should be rejected.

17 Claims, 3 Drawing Sheets

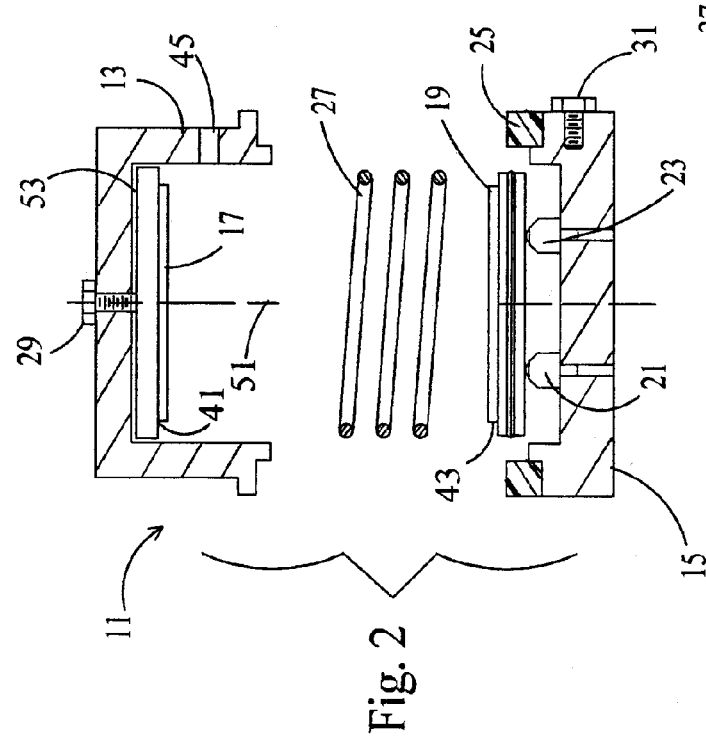
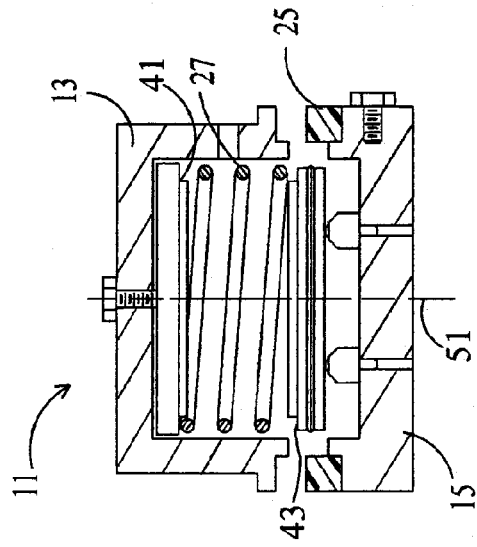
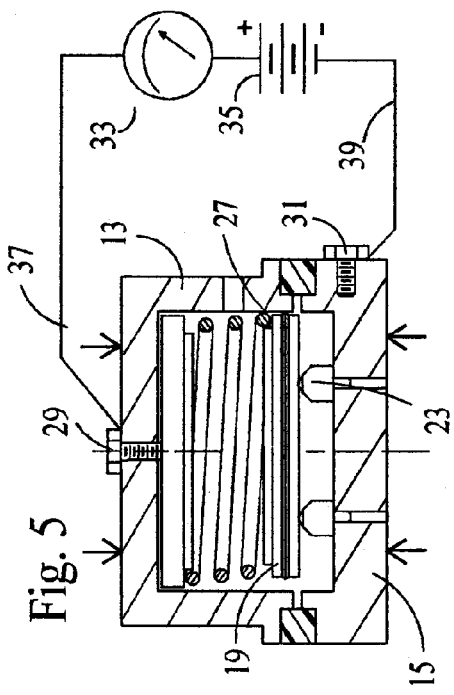
Fig. 2
Fig. 3
Fig. 4
Fig. 5

FIXTURE FOR TESTING SPRING SQUARENESS UNDER A LOAD

BACKGROUND OF THE INVENTION

1. Field of the Invention

The present invention relates generally to quality control systems and more particularly to a concentricity test fixture for helical springs and similar resilient members, and to a technique for assuring that a lot of such resilient members exhibits acceptable compressive attributes such as squareness of the ends under a load.

2. Description of the Related Art

It is desirable to monitor coil spring quality by checking for departure from a helical configuration and fixtures for accomplishing this for springs in their unstressed state is well documented. For example, U.S. Pat. No. 4,472,882 discloses a test fixture for measuring the squareness of unstressed coil springs by positioning a candidate spring adjacent a calibrated contoured surface of unique geometry and positioning the spring to touch the fixture at various locations. The patented arrangement does not address variations in spring squareness which might occur when the spring is compressed or stretched.

Departure from a truly helical configuration under load can have adverse effects. For example, in a mechanism having coil spring loaded poppet valves, excess departure can side-load the valve train increasing friction, affecting performance and decreasing wear life. The ability to test a coil spring or similar resilient member for squareness under load is a salient feature of the present invention.

SUMMARY OF THE INVENTION

The present invention provides solutions to the above identified problems by facilitating a measurement of a side load imparted by a coiled spring under stress when a first end and a second thereof are held parallel to one another.

The invention comprises, in one form thereof, a coil spring testing fixture having a pair of spaced apart spring end engaging jaws that are relatively movable toward and away from one another along a primary spring axis. One jaw is adapted to engage a first end of a spring and the other jaw is adapted to engage a second end of the spring to axially fix the ends relative to the respective jaws while allowing relatively free motion of one end relative to the other end in directions orthogonal to the primary spring axis. An electrical circuit detects excess motion of one end in directions orthogonal to the primary spring axis induced by motion of the jaws toward one another and the resulting compression of the spring. The first end of a spring is laterally restrained by the one jaw so that the second end and other jaw move together in directions orthogonal to the primary spring axis.

An advantage of the present invention is that it is simple to operate and provides an answer to the question of spring suitability.

Another advantage of the invention is that the fixture does not require optical comparators or other sophisticated equipment but uses a simple hand-held voltmeter with continuity checking capability to obtain information necessary to determine the acceptable characteristics of a spring.

A further advantage is that the same fixture may be adapted to various spring sizes by providing pairs of spring guides in pre-designed sizes.

BRIEF DESCRITPION OF THE DRAWINGS

FIG. 2 is a simplified partially cross-sectional view of FIG. 1 with the fixture in an opened position and ready to receive a spring for testing;

FIG. 3 is a simplified partially cross-sectional view of FIG. 1 wherein a spring to be tested is located within the fixture;

FIG. 4 is a simplified view of FIG. 1 that includes electrical components for evaluating a test for an acceptable spring under a compressive load;

FIG. 5 is a simplified view of FIG. 1 that includes electrical components for evaluating a test for an un-acceptable spring under a compressive load.

Corresponding reference characters indicate corresponding parts throughout the several drawing views.

DETAILED DESCRIPTION OF THE INVENTION

Figure 1:
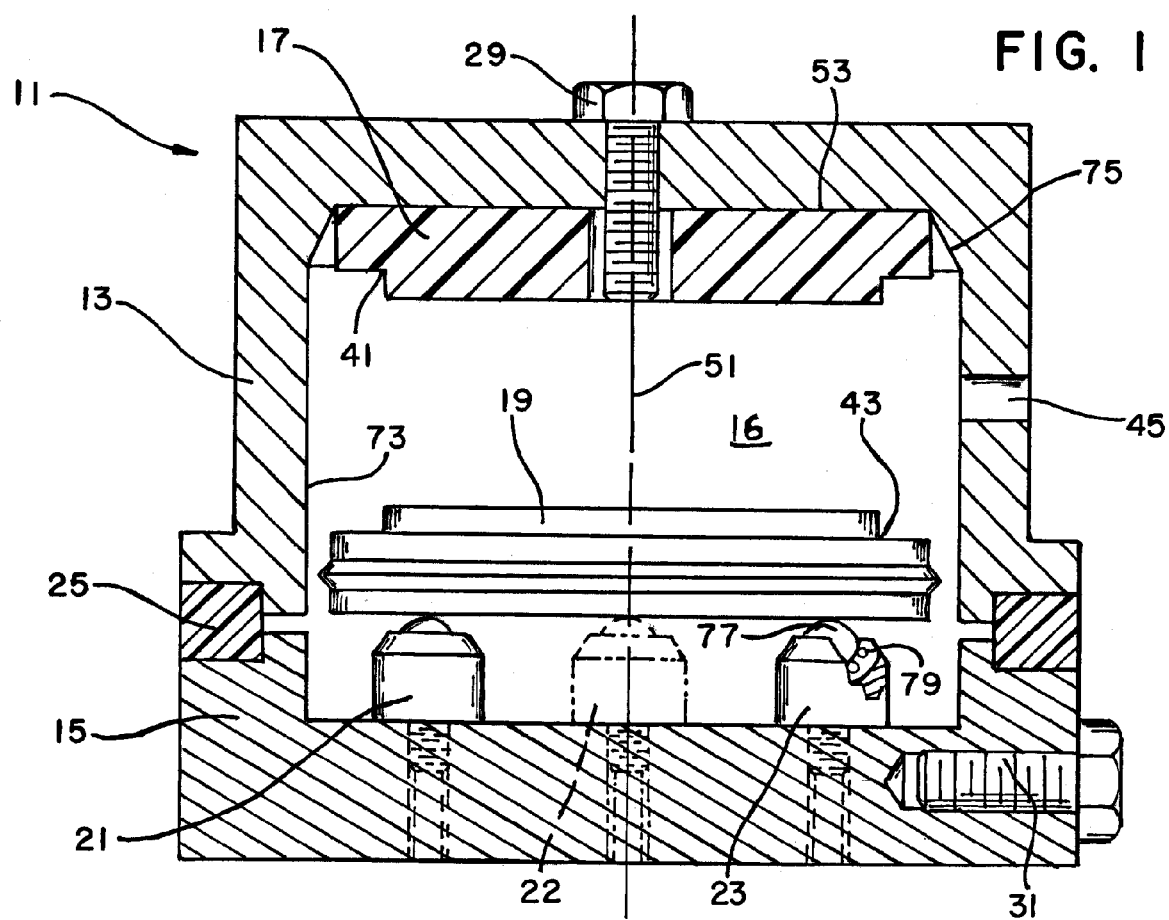
FIG. 1 shows a squareness under load test fixture, partially in cross-section, according to one form of the invention.

Referring now to the drawings and particularly to FIG. 1, there is shown an illustrative test fixture 11 for performing a simple "accept" or "reject" test for coil spring squareness under compressive load for a spring 27. The test fixture 11 includes a housing made of a top portion or cover 13 and a bottom portion or base 15. The top portion or cover 13 and a lower or base portion 15 are electrically conductive. However, the cover 13 contains a contoured insulative upper spring guide 17 while the base 15 for the housing supports a lower spring guide 19 that is located on a set of three equiangularly spaced low friction rollers, 21, 22 and 23 located on a same radii with respect to an axis 51 and are fixed to the base 15 to engage and support the lower spring guide 19. The configuration of the upper spring guide 17 is generally circular and is centered on the axis 51 by a tapering frustro conical region or surface 75 located in an upper section of interior sidewall 73 of cover 13. The upper spring guide 17 is rigidly fixed in place with respect to axial axis 51 through an adhesive interface 53, as illustrated in FIG. 2. The rollers 21, 22 and 23 provide a low friction electrically conductive support for the jaw or spring guide 19 and each may include a primary roller ball 77 supported in a ball bearing race illustrated at 79. The rollers 21,22, and 23 allow the lower spring guide 19 relatively free lateral movement within the cavity 16 formed within the housing fixture and may be made of stainless steel or similar electrically conductive material commercially available as Ball Transfer Units that are known and used in industry, for example, as photocopier slide supports.

A non-electrical conductive annular guide 25 functions to align the cover 13 and base 15 and provide electrical isolation from each other when they are closed on one another. A vent 45 is located in cover 13 to allow air to escape from within cavity 16 of the housing when the cover 13 is located on the base 15. The annulus guide 25 and the upper spring guide 17 may be made from a nylon, acrylic, or similar insulating material while the cover 13, base 15 and lower spring guide 19 are preferably made of a stainless steel or similar good conductive material. A screw 29 in cover 13 and a screw 31 in base 15 form electrical terminals to connect the electrically conductive portions of cover 13 and base 15 to a continuity testing arrangement such as shown in FIGS. 4 and 5.

Except for the screw 31 and vent 45, the cover 13, base 15, guide 17 and guide 19 of the fixture of FIG. 1 exhibit cylindrical symmetry about axis 51. Of course, the exterior of the fixture may depart from such symmetry, for example, for manufacturing convenience, or to suit a specific installation. The interior sidewall portion 73 of cover 13 and the peripheral portion of lower spring guide 19 are also preferably cylindrically symmetric with respect axis 51 to insure that a resulting test for angular spring orientation of a spring to be tested independent. Note, that the lower spring guide 19 is spaced a peripherally uniform distance from the inner cylindrical sidewall 73 of the cover 13 and is not restrained in that position, but rather is free to move in any direction orthogonal to the axis 51 on the rollers 21, 22 and 23 until spring guide 19 comes in contact with the cylindrical sidewall 73.

In FIG. 2, cover 13 and base 15 are shown as having been moved axially away from one another to accept a spring 27 that has been selected from a spring lot. A selected spring 27 is precisely located to have its axis collinear with the fixture axis 51 by annular groove 41 on spring guide 17 and annular groove 43 on spring guide 19. The annular groove 41 acts as a jaw to fix an end of spring 27 to the upper spring guide 17 while annular groove 43 acts as a jaw to fix an opposite end of spring 27 to the lower spring guide 43 such that initially spring 27 is located along the fixture axis 51, as illustrated in FIG. 3, when the cover 13 and base 15 begin to close on one another. Continued closure of the cover 13 and base 15 is achieved by a compressive force being applied to cover 13 and base 15, as illustrated by arrows 47 and 49 in FIG. 4 to compress the spring 27 with a preferred stress. When the structure in FIG. 2 is compared with that of FIG. 4, it should be apparent that the cover 13 and base 15 and respective supported spring guides 17 and 19 movable along the fixture axis 51 between the open position for accepting a spring 27 to a closed position wherein spring 27 is compressed. In an acceptable coil spring 27, the lower spring guide 19 is retained in the generally cylindrical cavity 16 defined by side wall 73 of the cover 13 as shown in FIG. 4.

In FIGS. 4 and 5, an electrical circuit including a galvanometer 33, battery 35 and leads 37 and 39 is shown as being connected with screw 29 in cover 13 and screw 31 in base 15. A simple volt/ohm meter or continuity tester as well as any other suitable indicator and/or power source could function in a similar manner to achieve a similar result. If the spring 27 is square (does not exhibit any induced stress in directions perpendicular to the primary fixture axis 51), the lower spring guide 19 remains centered on the fixture axis 51 as shown in FIG. 4. So long as the lower spring guide 19 is located as in FIG. 4, there is no current flow through an indicator such as galvanometer 33 from battery 35 by way of the leads 37 and 39 attached to cover 13 and base 15 because of an open circuit is located between cover 13 and base 15 as represented by the gaps 81 and 83. However, should the compressive stress 47, 49 induce a lateral stress in spring 27, the lower spring guide 43 is free to move in directions orthogonal to the fixture axis 51 and the spring 27 will experience a resulting lateral strain that moves the lower spring guide 19 toward the cylindrical sidewall 73 of cover 13. A sufficient lateral travel component in spring 27 will cause the lower spring guide 19 to contact and make an electrical connection with the inner surface of cylindrical sidewall 73, see FIG. 5, to close the circuit and enabling an indicator such as galvanometer 33 to inform an operator that the spring 27 is not square and should be rejected as not possessing a desired squareness characteristic.

Figure 6:
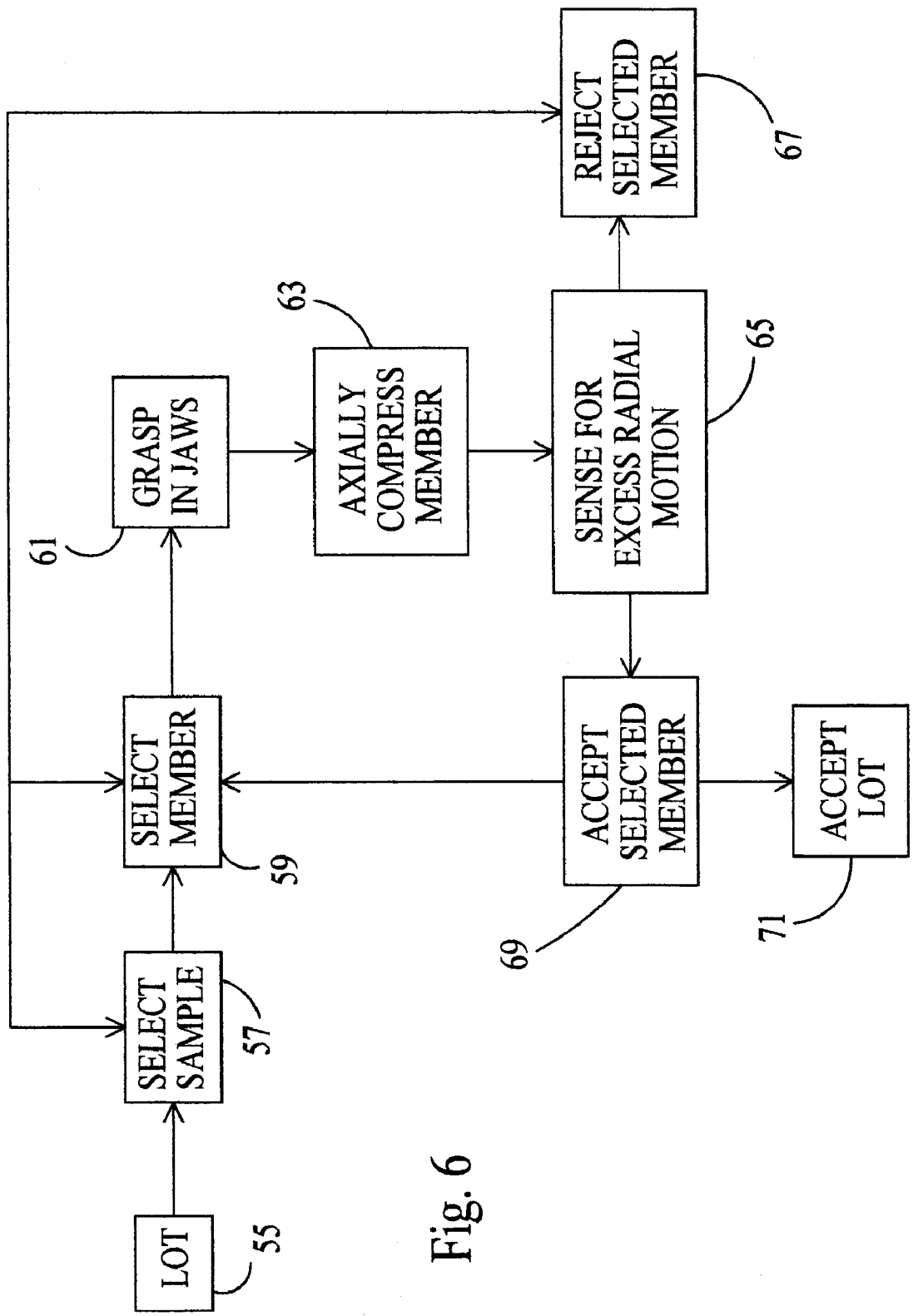
FIG. 6 is a flow chart illustrating a process for sampling a lot or supply of springs for squareness.

The process of determining spring squareness of a spring 27 of the present invention is set forth in the flow chart of FIG. 6 when viewed in conjunction with the structure illustrated in FIGS. 2–5. In this process, a sample spring 27 is randomly selected from a lot or supply of springs 55, as indicated at by step 57. The number of sample springs 27 selected for testing or sample size may be determined by statistical considerations such as lot size and the desired degree of confidence as to the acceptability of the lot 55 based on acceptability of individual tested springs. An individual spring of the number selected to be sampled is indicated by step 59. Of course, the lot may be sufficiently small such that an individual spring 27 may comprises the entire selected sample. Step 61 indicates the selected spring 27 has been gripped by the jaws or spring guides 17 and 19 in a manner as shown in FIG. 3. A compressive force 47, 49 is then applied to cover 13 and base 15 to axially compress the selected spring 27 as illustrated in FIG. 4 and shown by step 63 in FIG. 6. Excess radial motion is sensed for by the electrical circuit through step 65 and, if such radial motion is detected as illustrated in FIG. 5, a spring is rejected as indicated by step 67. Otherwise, the lower end of a spring 27 and lower jaw or spring guide 43 remain spaced from the surface sidewall 73 as illustrated in FIG. 4, the indicator 33 remains un-energized and the spring 27 is accepted as shown at 69. Once a spring 27 has been rejected, another spring 27 from the selected number 59 in the sample or lot 55 for testing, a new sample (which may comprise the entire lot) may be selected from the lot 55, or the entire lot may be rejected as excessively "un-square." If a spring 27 that is first selected is accepted as indicated at 69, further springs 27 may be selected from the number to be tested until the sample select number 59 has been exhausted. Acceptance of an entire sample (or a statistically determined percentage of the sample) dictates acceptance of the entire number of springs in the lot 55 as shown at 71. If the test is particularly critical (as dictated by a particular application, spring compression force 47, 49, and the dimensions of gap 83), rejecting a single spring 27 my dictate an entire lot 55 must be tested and only those individual springs that pass the test for squareness of the above process be retained as acceptable.

What is claimed is:

1. A process of inspecting a lot of resiliently compressible members to determine whether the members of the lot exhibit acceptable compressive attributes, comprising the steps of:

selecting a sample of at least one member from said lot;
grasping the selected member of the sample between a pair of spaced apart jaws;
subjecting the grasped member to a controlled compressive stress along a primary axis;
sensing for induced stress in the selected member in directions generally perpendicular to the primary axis; and
rejecting the selected member as having unacceptable compressive attributes if the sensed stress exceeds a predetermined threshold.

2. The process of claim 1, including the additional steps of:

repeatedly performing the steps of grasping, subjecting, sensing and rejecting for at least a second member in the selected sample; and
accepting the lot only if no member of the selected sample is rejected.

3. The process of claim 2, wherein the repeated step of selecting selects a sample including all members of the lot not previously selected whenever a previously selected member is rejected.

4. The process of claim 2, wherein the repeated step of selecting selects a sample including all members of the lot not previously selected and the members not previously selected are individually accepted or rejected.

5. The process of claim 2, wherein the repeated step of selecting selects a sample including less than all remaining members of the lot, and the additional step of repeating the steps of selecting, grasping, subjecting, sensing, rejecting and repeatedly performing on the lot continues until no member of the selected sample is rejected whereupon the lot is accepted.

6. The process of claim 1, wherein the step of sensing for induced stress in a selected member comprises detecting a resulting strain in directions generally perpendicular to the primary axis.

7. The process of claim 6, wherein the step of sensing for induced stress in the selected member includes gripping a first end of said selected member with a first jaw to provide the compressive force and preclude motion in directions orthogonal to the primary axis while gripping a second end of said selected member with a second jaw to provide the compressive force and allow relatively free member motion in directions orthogonal to the primary axis.

8. The process of claim 7 wherein said step of sensing for induces stress further includes the step of indicating when the orthogonal movement of said second end closes an electrical circuit to inform an operator of an unacceptably selected member.

9. A coil spring testing fixture, comprising:
a spring having a first end and a second end;
a first spring guide and a second spring guide that are spaced apart for each other in said testing fixture and movable toward and away from each other along a primary axis of said fixture, said first spring guide receiving said first end of said spring and said second spring guide receiving said second end of said spring, said first spring guide holding said first end in a substantially fixed axial position while said second spring guide allowing relatively free motion of said second end of said spring relative to said first end of said spring end in directions orthogonal to the primary axis of said fixture, said second end of said spring is laterally restrained by said second spring guide so that said second end and said second spring guide move together in directions orthogonal to the primary axis of said fixture;
an electrical circuit for detecting excess motion of said second end in directions orthogonal to the primary axis induced by motion of said first and second spring guides toward one another and a resulting compression of said spring; and
a set of low friction roller for engaging and supporting said second spring guide.

10. The fixture of claim 9, further comprising first and second electrically conductive housing portions with at least the second housing portion having a relatively cylindrical cavity, said housing portions respectively supporting said first and second spring guides and relatively movable therewith along said primary axis between an open position for accepting said spring and a closed position in which the said second guide is located within the generally cylindrical cavity.

11. The fixture of claim 10, wherein said second spring guide and second housing portion are rigidly joined while said first housing portion that axially supports the said first spring guide while allowing said second spring guider to have relatively free lateral movement.

12. The fixture of claim 10, further comprising an insulating annulus interposed between said first and second housing portions to maintain electrical isolation there between.

13. The fixture of claim 10, further comprising a set of electrically conductive low friction roller supports fixed to said second housing portion for engaging and supporting said second spring guide.

14. The fixture of claim 13, wherein the electrical circuit includes the set of roller supports, said first and second housing portions and said second spring guide.

15. A process of testing a coil spring from a supply of springs, each coil spring having an unstressed generally helical configuration for excess departure from a helical configuration under compressive load, comprising:
radially fixing a first end of a first spring;
axially compressing said spring while allowing a second end of said spring have relatively free radial motion and rollingly supporting said second spring end to allow omni-directional transverse motion while axially compressing said first spring; and
sensing when compression induced radial motion of said second end exceeds a predetermined threshold.

16. The process of claim 15, wherein the step of sensing includes determining when lateral movement of said second end closes a normally open sensing circuit.

17. The process of claim 15, including the additional steps of rejecting said first spring when the induced radial motion of said second end exceeds the predetermined threshold, and repeating the steps of radially fixing, axially compressing and sensing on at least a second spring from the supply of springs.

* * * * *